(12) United States Patent
Bernet et al.

(10) Patent No.: US 9,207,251 B2
(45) Date of Patent: Dec. 8, 2015

(54) USER INTERACTION WITH AUTOMATED ANALYTICAL APPARATUS

(75) Inventors: Roland Bernet, Immensee (CH); Robert Huesler, Root (CH); Raymond Ochsenbein, Zurich (CH); Johann Florian Wassermann, Horgen (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 13/397,899

(22) Filed: Feb. 16, 2012

(65) Prior Publication Data

US 2013/0043361 A1    Feb. 21, 2013

(30) Foreign Application Priority Data

Apr. 19, 2011  (EP) .................................... 11163032

(51) Int. Cl.
*G01N 21/00*  (2006.01)
*G01N 35/00*  (2006.01)

(52) U.S. Cl.
CPC .. *G01N 35/00722* (2013.01); *G01N 2035/0091* (2013.01); *G01N 2035/00891* (2013.01)

(58) Field of Classification Search
CPC .................. G01N 35/0063; G01N 2035/0091; G01N 35/00; G01N 2035/00891
USPC ........ 248/274.1; 422/68.1, 99, 400; 435/91.1, 435/303.1
See application file for complete search history.

(56) References Cited

U.S. PATENT DOCUMENTS

| | | | |
|---|---|---|---|
| 2008/0063570 A1* | 3/2008 | Fujino .............. | G01N 35/00663 422/400 |
| 2009/0117620 A1* | 5/2009 | Fritchie ................ | B01L 3/5085 435/91.1 |
| 2012/0269604 A1* | 10/2012 | Baumann ............... | G01N 35/04 414/222.01 |

FOREIGN PATENT DOCUMENTS

| | | |
|---|---|---|
| DE | 19535039 A1 | 3/1996 |
| DE | 19535039 C2 | 3/1996 |
| DE | 10041230 A1 | 3/2002 |
| EP | 0549905 A1 | 7/1993 |
| EP | 0549905 B1 | 7/1993 |
| EP | 12155892 | 4/2012 |
| JP | 10227797 A | 8/1998 |
| JP | 2010223810 A | 10/2010 |
| WO | 2010056903 A1 | 5/2010 |

OTHER PUBLICATIONS

Abbott, "Architect ci8200" product information, accessed from the internet on Feb. 12, 2012 at http://www.ilexmedical.com/products.php?id=13&prt=1.
Abbott, 2009, "PRISM nEXT" product brochure.
Beckman Coulter, 2006, "UniCel R DxC 600i Synchron R Access R Clinical System", product brochure.

(Continued)

*Primary Examiner* — Todd M Epps
(74) *Attorney, Agent, or Firm* — David J Chang

(57) ABSTRACT

A method of interaction between an automated analytical apparatus for performing an analytical process and a user is disclosed comprising displaying all features necessary for performing the analytical process on a display which is mounted on the apparatus.

13 Claims, 5 Drawing Sheets

(56) References Cited

OTHER PUBLICATIONS

Johnson&Johnson Ortho-Clinical Diagnostics, 2005, "VITROS R 350", product brochure.

Siemens, "ADVIA Centaur R XP Immunoassay System" product information, accessed from the Internet on Feb. 13, 2012 at http://www.medical.siemens.com/webapp/wcs/stores/PrintableView?locale=en_INTDIAG . . . .

* cited by examiner

USER INTERACTION WITH AUTOMATED ANALYTICAL APPARATUS

CROSS-REFERENCES TO RELATED APPLICATIONS

The present application claims the benefit of priority under 35 U.S.C. §119(a) of EP11163032.3, filed Apr. 19, 2011, the entire contents of which is hereby incorporated by reference.

FIELD OF THE INVENTION

The present invention relates to user interaction with an automated analytical apparatus.

BACKGROUND OF THE INVENTION

Automated analytical apparatuses are well known in the art. Such apparatuses often comprise displays for interaction of the user with the apparatus. Commonly, displays for user interaction with automated analytical apparatuses are mounted with movable arms with a single fixed attachment site on the analyzer. Such analyzers often comprise additional lights, sensors and/or acoustic signals on the apparatus that control parts of the actions required for performing the analytical process.

The present invention provides an improved user interaction with an automated analytical apparatus via display.

SUMMARY OF THE INVENTION

The present invention relates to a method of interaction between an automated analytical apparatus for performing an analytical process in at least one analytical module, and a user, said method comprising displaying all features necessary for performing said analytical process on a display, wherein said display is mounted in front of said automated analytical apparatus. The mount of said display is constructed and arranged to move the display laterally along at least one of said modules. Moving the display into a position overlapping with a module, prevents access to the module. Moving the display into a position not overlapping with a module enables access to the module.

The present invention also relates to a fully automated analytical apparatus comprising at least one module for performing an analytical process, a control unit and a display, wherein said display is mounted in front of said analytical apparatus and wherein said mount of said display is constructed and arranged to move the display laterally along at least one module of said apparatus. When the position of the display overlaps with a module, access to the module is prohibited and when the display is located in a non-overlapping position of said module, access to said module is enabled. All features necessary for performing said analytical process are displayed on said display.

DETAILED DESCRIPTION OF THE INVENTION

Figure 1:
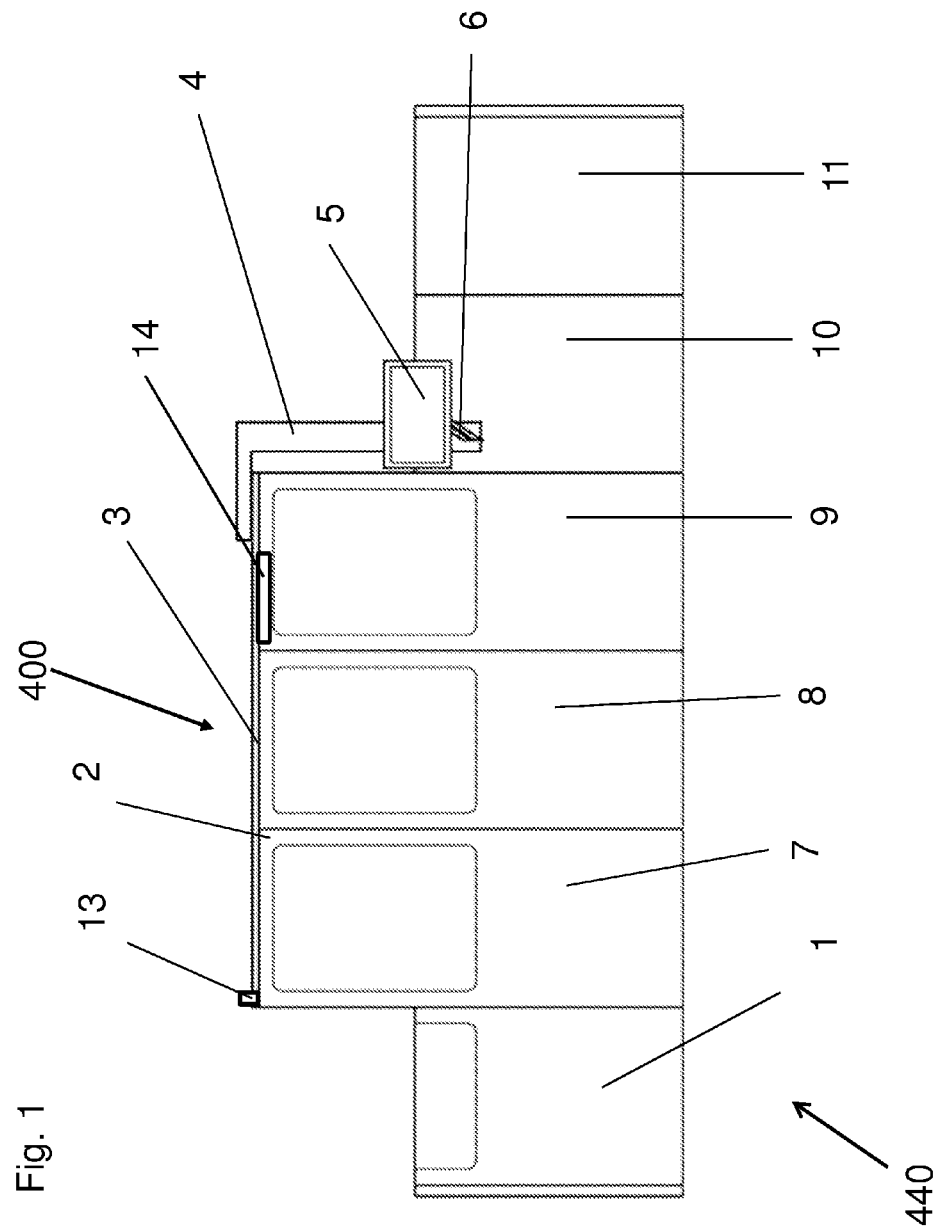
FIG. 1 shows a system comprising an analytical apparatus with a preanalytical module and several analytical modules. A display is attached to a rail which is mounted on top of three of the modules.

The present invention relates to a method of interaction between an automated analytical apparatus for performing an analytical process in at least one analytical module, and a user, said method comprising displaying all features necessary for performing said analytical process on a display, wherein said display is mounted in front of said automated analytical apparatus. The mount of said display is constructed and arranged to move the display laterally along at least one of said modules. Moving the display into a position overlapping with a module, prevents access to the module. Moving the display into a position not overlapping with a module enables access to the module.

This has the advantage that all user interaction relating to performing the analytical process can be guided entirely by the display. A further advantage is that the display, which is mounted in front of the analytical apparatus and can be moved laterally along at least part of said apparatus can be brought into a position close to the module which needs to be accessed by the user without interfering with access. Accessing may e.g. opening of a stacker and loading of consumables, or loading of reagent containers into the apparatus. As the display is mounted such that it is positioned in front of the apparatus, access of the module in front of which the display is located cannot be accessed from the front. Positioning of the display in a non overlapping position can be achieved as described herein. During moving and in any position in front of the apparatus, the display always displays all features necessary for performing the analytical process. The display may also be moved sideways in one end position to enable access to a module.

In one embodiment, the analytical apparatus comprises a module for loading sample vials onto the analytical apparatus. This module is considered a pre-analytical module, and the process of loading sample vials into the analyzer is considered a pre-analytical process, as opposed to an analytical process, which relates to processes such as liquid transfer, transfer of receptacles in which processing of a sample occurs, reactions etc. The interaction between any pre-analytical module and the analytical apparatus may be performed via the display, or such interaction may be autonomous. Thus, "all features necessary for performing an analytical process" relates to the analytical processes herein described, not to pre-analytical processes. However, the features necessary for performing the analytical process also comprise processes such as loading of reagents and consumables which are required to perform the analytical process.

The term "module" as used herein relates to any spatially defined location within the analyzer. Two modules (e.g. 8,9) can be separated by walls, or can be in open relationship. Any one module (7,8,9,10,11) can be either autonomously controlled, or control of the module (7,8,9,10,11) can be shared with other modules (7,8,9,10,11). In one embodiment, all modules (7,8,9,10,11) are controlled centrally. Transfer between modules (7,8,9,10,11) can be manual or automated.

The term "in front of said automated analytical apparatus" is meant to refer to the side of the analytical apparatus where the user interaction during operation of the analytical apparatus occurs. Interaction with the analytical apparatus for maintenance or repair when the analytical apparatus is not in operation may also occur on other sides than the front of the automated analytical apparatus.

Displays are well known in the art. In one embodiment, the display (5) comprises a touchscreen (5a).

One analytical process comprises reacting an analyte with a compound. The term "reacting" as used herein relates to any type of chemical reaction of the analyte with reagents that is necessary to obtain a detectable signal. In one embodiment, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

Another analytical process comprises isolating and separating an analyte from other other material.

Figure 2:
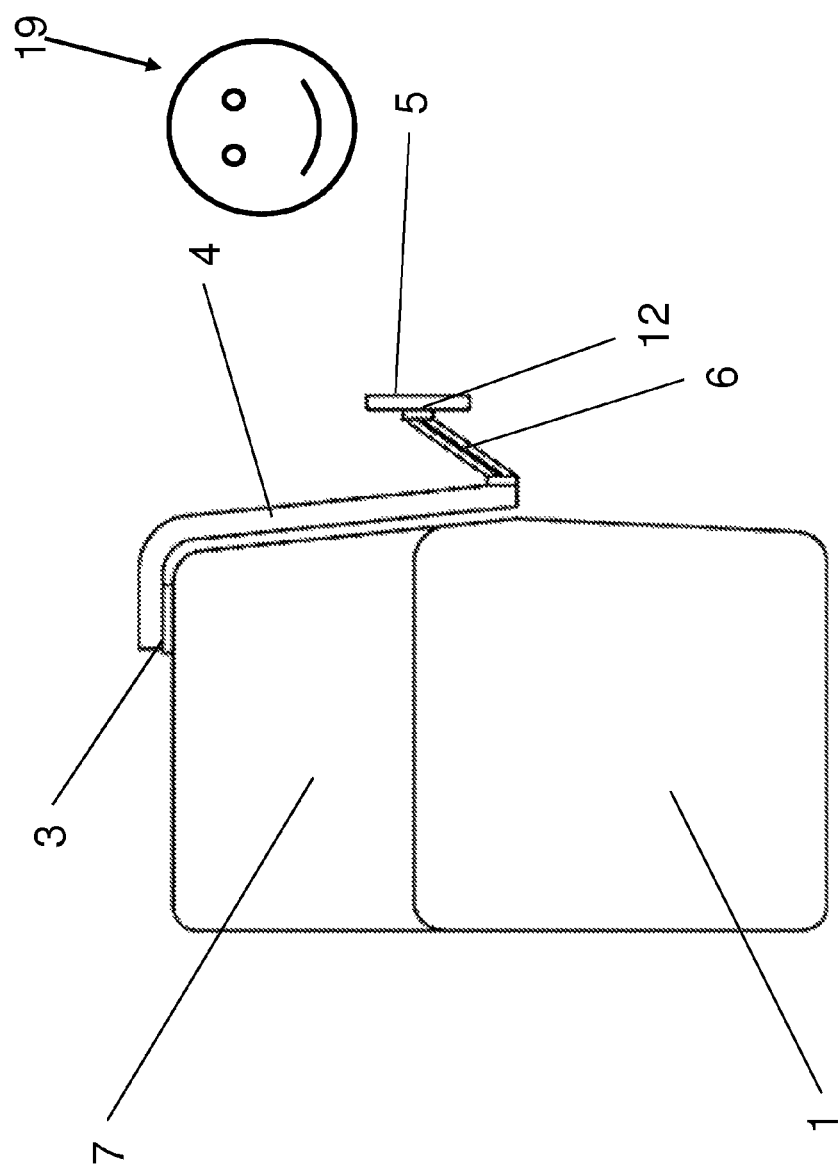
FIG. 2 shows a side view of the apparatus with the device attached to a first and a second arm, and a pivot for adjusting the position of the display for optimal user interaction.

In one embodiment of said method herein described, the mount of said display is constructed and arranged to move the display laterally along at least one of said modules. In one embodiment, the display (5) is mounted on a rail (3) which extends along the front of the top side of at least one module (7,8,9), see FIGS. 1 and 2. The display (5) can be moved along the rail (3), resulting in a horizontal movement of the display (5) along the at least one module (7,8,9,10,11). In one embodiment, the rail (3) extends along at least two modules (7,8).

In one embodiment of the method herein described, the method comprises accessing a module (e.g. 7), wherein said display is moved to a position not overlapping with said module (7). In one embodiment, when the rail (3) extends along at least two modules (e.g. 7 and 8), the display is moved to a second module (8) in order to access the first module (7).

Figure 5:
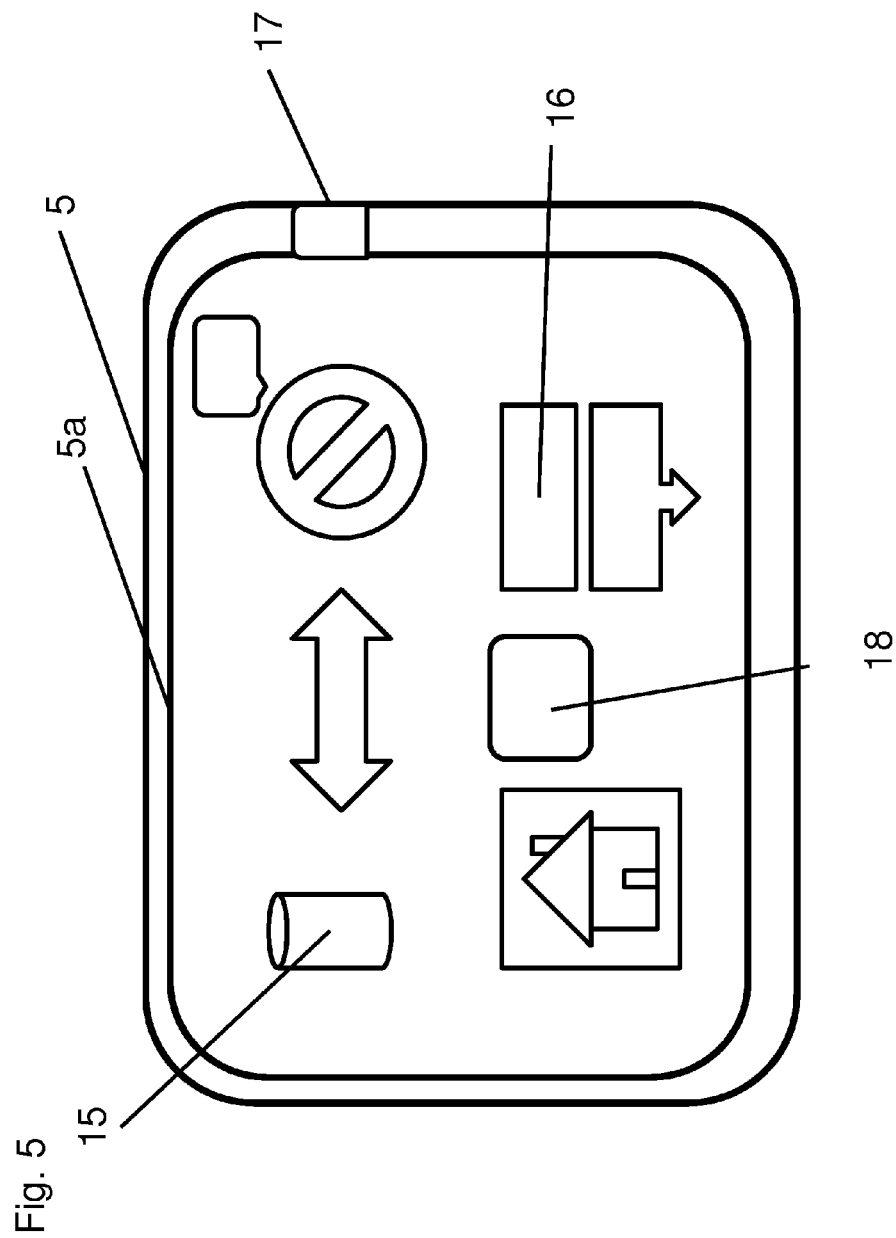
FIG. 5 shows a display with a touch screen and different features displayed thereon for user interaction with the analytical system.

Specifically, features (15) displayed by said display comprise the loading status (15) of the apparatus (400), and/or the loaded consumable amount, and for information on when the modules are accessible for loading or unloading of consumables and/or reagents (16). An exemplary display (5) with features (15) is shown in FIG. 5.

The advantage of displaying all features necessary for performing the analytical process is that the user can control the analytical process entirely from the display. Although the apparatus may additionally comprise optional lights or indicators for easier and quicker identification of the part of the apparatus requiring action, the display allows controlling all modules required for performing the analytical process in the analytical apparatus from the display. Thus, the user does not need to check controls in different locations of the apparatus before performing an action. This makes it easier for the user to safely operate the analytical apparatus.

Figure 3:
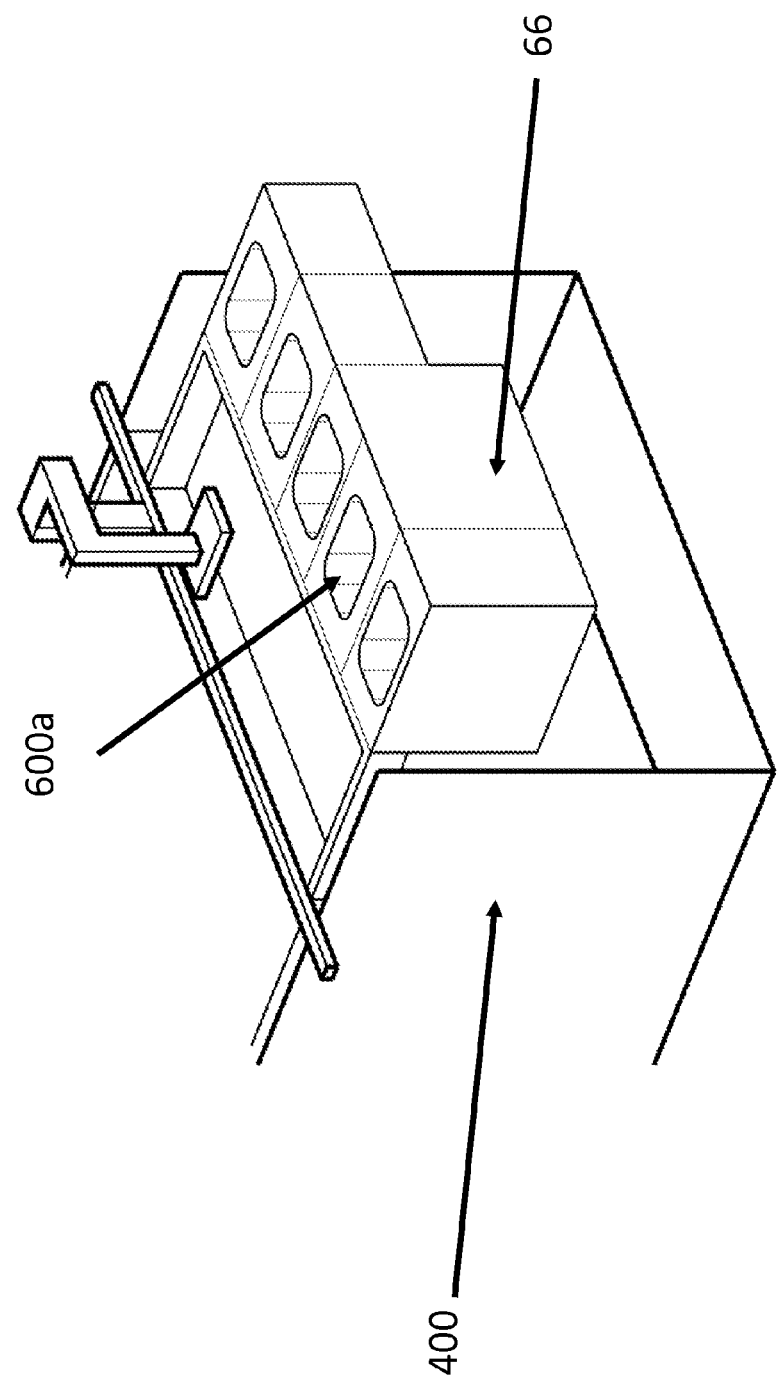
FIG. 3 shows a drawer of the analytical apparatus.

Specific actions controlled by said display comprise unlocking a drawer by requesting drawer unlock via the display (5). A drawer is, in one embodiment, a drawer comprising a stacker unit (66) for loading and stacking consumables. A user interface (16) on the display (5) to display loading step guidance of stacker units (66) may also be included (see FIG. 3). One stacker unit may comprise at least one stacker (600). Further specific actions are: automatic opening of housing (2), wherein a request for opening and action to open the housing (2) are entered and controlled via the display (5). In one embodiment, a button (17) on the side of the display (5) is present (see FIG. 5), wherein said button (17) has to be engaged simultaneously with a button (18) on the touchscreen of the display (5). This requires the user (19) to use both hands, thus reducing the risk of opening the lid accidentally, and prevents the user from being close to the automated door.

Figure 4:
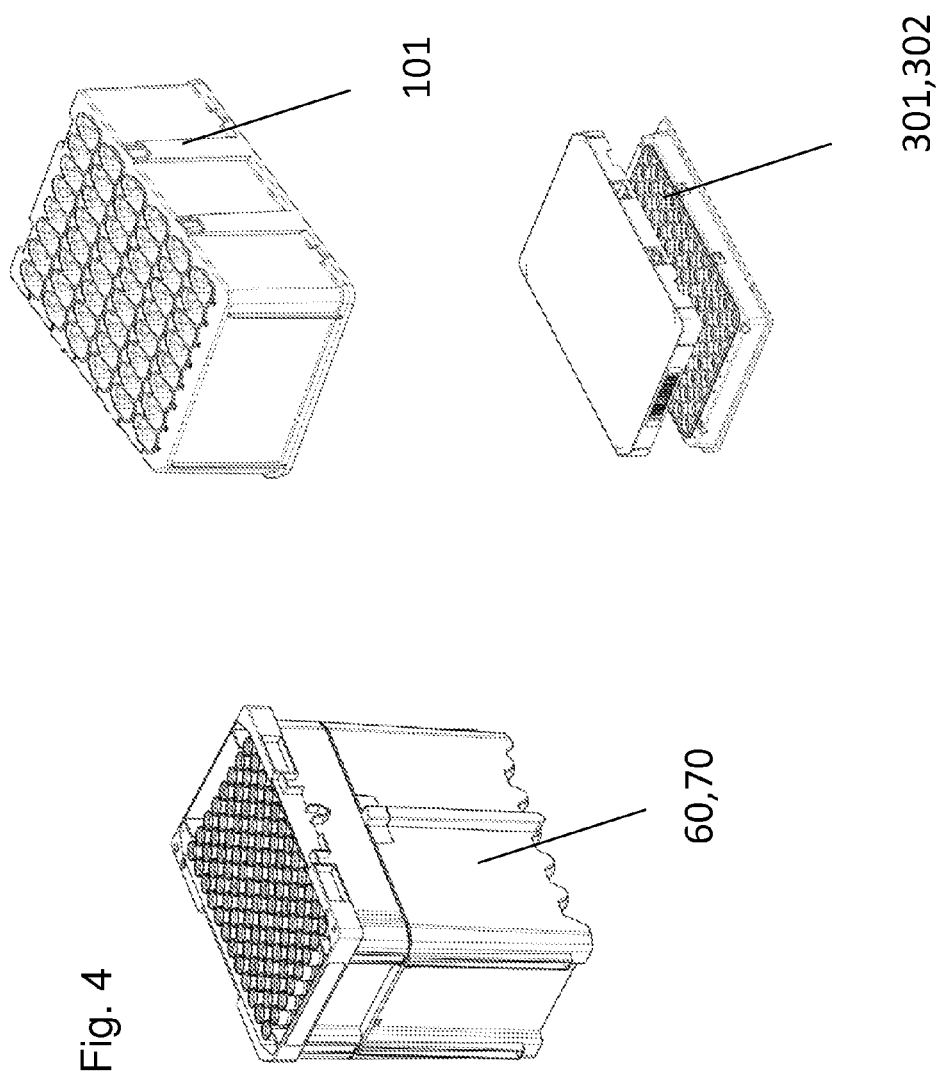
FIG. 4 shows exemplary consumables.

The term "consumables" relates to plastic consumables for storing other consumables, such a pipette tips or single tubes, of for holding reagents and samples, or consumables (101, 301,302) holding reaction mixes in which the processing or analyzing of the analyte are performed. Embodiments of such consumables include racks (60, 70) or multiwell plates (101, 301,302), see FIG. 4. Different types of multiwell plates (101,301,302) with identical footprint can, in one embodiment, be used in the system (440). Such types of multiwell plates (101,301,302) are multiwell plates for storing samples or reagents, multiwell plates for isolating and analyzing an analyte, and/or multiwell plates for reacting an analyte to obtain a detectable signal. In one embodiment, if the analyte is a nucleic acid, the reacting may be any type of amplification of nucleic acids known to the person skilled in the art. In one embodiment, said consumables (60, 70, 101,301,302) comprise at least one tip rack (60, 70) and one multiwell plate (101, 301). In one embodiment, said footprint comprises a length and width of the base corresponding to ANSI SBS footprint format. In one embodiment, the length is 127.76 mm +/− 0.25 mm, and the width is 85.48 mm +/− 0.25 mm.

According to the method of the present invention, control and operation of at least the analytical part of the apparatus are fully managed via said display. In one embodiment, additional control devices are absent. In another embodiment, supplementary optional control lights and/or light barriers are present on selected parts.

Further specific features displayed by the display comprise walk-away time until reload of the apparatus, and/or displaying next required user action by showing differently colored time windows for different user action on said display. In one embodiment, the analytical process is not stopped during reloading of the apparatus. The timing of the reload is, thus, defined solely by the requirement for new consumables or reagents, but not by the status of the analytical process.

Further features can be comprised on said display which are either required for controlling the function of the automated analytical apparatus or provide the user with information which allows optimization of walk-away time.

The present invention also relates to a fully automated analytical apparatus (400) comprising at least one module (7,8,9) for performing an analytical process, a control unit (14) and a display (5), wherein said display (5) is mounted in front of said analytical apparatus (400) and wherein said mount of said display (5) is constructed and arranged to move the display (5) laterally along at least one module (7,8,9) of said apparatus (400). When the position of the display (5) overlaps with a module (7,8,9), access to the module (7,8,9) is prohibited and when the display (5) is located in a non-overlapping position of said module (7,8,9), access to said module(7,8,9) is enabled. All features (15) necessary for performing said analytical process are displayed on said display (5). In one embodiment, the mount of the display (5) is coupled to at least one guiding rail (3) or rails (3) on at least one module of said apparatus (400). In one embodiment the mount (4) of the display (5) is coupled to a double rail (3).

In one embodiment, the mount of said display may be coupled to an upper track for guidance, specifically, a cable conduit, and a lower track.

In one embodiment, the upper track or rail (3) comprises an arrestor (13) at least at one end of the at least one module. This arrestor (13) allows arrest of the display in the end position. In one embodiment, the display mount is rotatable to the side of the modules. This allows rotation of the display to the side to not block doors that need to be accessed.

In one embodiment of the mount of the display, the mount comprises a first arm (4), wherein said first arm (4) is connected to the rail (3), and a second arm (6), wherein said second arm (6) is connected to said first arm (4), comprises a pivot (12) to which the display (5) is connected. The pivot (12) permits lateral adjustment of the display (5). The connection between pivot (12) and display (5) is constructed and arranged to allow vertical/incline adjustment of the display (5). This has the advantage that the display (5) can be adjusted vertically for optimal reach by the user (19), and for providing free access to the bottom level for loading and unloading.

In one embodiment, the analytical apparatus may comprise additional pre-analytical modules (1). Pre-analytical modules are modules which do not participate in the analytical process. Such pre-analytical modules may be modules which sort sample tubes, provide sample tubes comprising samples to be analyzed to the analytical modules. The rail (3), in this embodiment, may run along all modules (1, 7, 8, 9, 10, 11), or it runs only along the top of modules (7, 8, 9, 10, 11) or only along one or more modules comprising a separation station (7,8,9). A "separation station" is understood to be a station where an analyte is separated from a solid support. In one embodiment, the processing area comprises a station for isolating an analyte.

The display (5) may be provided with or without a keyboard. In one embodiment, the display (5) is non-detachable.

In one embodiment, the apparatus unit recognizes which drawer is open and the control unit (14) of the apparatus controls the automatic movement of the display (5) to a position where action is required. This has the advantage that the user does not need to first go to the display (5) and move it to an appropriate position to carry out a task, but can immediately go to the display (5) and take care of the required action. The display (5) may also recognize its position along the system (440) and display (5) context and/or position related information. The display (5) may also automatically recognize where an action is required and automatically move to the respective position.

The invention claimed is:

1. A method of interaction between an automated analytical apparatus comprising at least one module for performing an analytical process, and a user, said method comprising;
displaying all features necessary for performing said analytical process on a display, wherein said display is mounted in front of said automated analytical apparatus, wherein said mount of said display is constructed and arranged to move the display laterally along said at least one module, and
moving the display laterally into a position overlapping with said at least one module, whereby access to said module is prevented, and wherein access to said module is enabled when moving the display into a position not overlapping with said module.

2. The method according to claim 1, further comprising: accessing said at least one module by moving said display to a position not overlapping with said module.

3. The method according to claim 1, wherein said displaying step further comprises displaying the loading status of the apparatus.

4. The method according to claim 1, wherein said displaying step further comprises displaying the loaded consumable amount.

5. The method according to claim 1, wherein said displaying step further comprises displaying information on when the modules are accessible for loading or unloading of consumables or reagents or both consumables and reagents.

6. The method according to claim 1, comprising unlocking a drawer by requesting drawer unlock via the display.

7. The method according to claim 1, further comprising: managing control and operation of the apparatus via said display.

8. The method according to claim 7, wherein said managing step requires no additional control devices.

9. The method according to claim 1, comprising displaying walk-away time until reload of the apparatus.

10. The method according to claim 1, comprising displaying next required user action by showing differently colored time windows for different user action on said display.

11. An automated analytical apparatus comprising at least one module for performing an analytical process, a control unit and a display, wherein said display is mounted in front of said analytical apparatus, wherein said mount of said display is constructed and arranged to move the display laterally along said at least one module of said apparatus, wherein, when the position of the display is overlapping with said at least one module, access to said module is prohibited and when the display is located in a non-overlapping position with said at least one module, access to said module is enabled, and wherein all features necessary for performing the analytical process are displayed on said display.

12. The analytical apparatus of claim 11, wherein said mount of said display is coupled to a guiding rail on said at least one module of said apparatus.

13. The analytical apparatus of claim 12 wherein said guiding rail is mounted on top of said at least one module.

* * * * *